United States Patent [19]

Eckols

[11] 4,012,504
[45] Mar. 15, 1977

[54] IODINE MINERAL OIL SOLUTION FOR PREVENTING BOVINE MASTITIS
[75] Inventor: Clyde S. Eckols, Kenedy, Tex.
[73] Assignee: Velvet Chemical Co., Kenedy, Tex.
[22] Filed: June 30, 1975
[21] Appl. No.: 591,940

Related U.S. Application Data

[63] Continuation-in-part of Ser. No. 252,746, May 12, 1972, abandoned, which is a continuation-in-part of Ser. No. 194,007, Oct. 29, 1971, abandoned.
[52] U.S. Cl. .............................. 424/150; 424/312
[51] Int. Cl.$^2$ ....................................... A61K 33/18
[58] Field of Search ................................... 424/150

[56] References Cited
OTHER PUBLICATIONS

Clark — J. Am. Pharm. Assn., vol. 8, (1919), pp. 611 and 612.
Anon — Chem. Abst., vol. 12, (1918), p. 2409[8].
Westen et al. — J. Dairy Science, vol. 53, (1970), pp. 1391–1394.
Schwartz et al. — Surface Active Agents & Detergents, vol. 2, (1958), p. 128.

Primary Examiner—Sam Rosen
Attorney, Agent, or Firm—Clarence A. O'Brien; Harvey B. Jacobson

[57] ABSTRACT

A solution of iodine in mineral oil is externally applied to cow teats to control the spread of bovine mastitis and to heal chapping and chafing. The composition is made by agitating elemental iodine in heated mineral oil until it dissolves. An improved teat dip includes, in addition to the mineral oil and iodine, a small quantity of polyoxyethylene cetyl ether.

16 Claims, No Drawings

IODINE MINERAL OIL SOLUTION FOR PREVENTING BOVINE MASTITIS

This application is a continuation-in-part of my earlier copending application, Ser. No. 252,746, filed May 12, 1972, now abandoned which earlier application was a continuation-in-part of Ser. No. 194,007, filed Oct. 29, 1971, now abandoned.

BACKGROUND OF THE INVENTION

This invention relates to a method for treating dairy cows to control bovine mastitis and to a composition useful therein.

The repeated milking of large herds of dairy cows as practiced by the modern-day dairy industry promotes the spread of various cattle diseases. One such disease known as "bovine mastitis" is caused by exposure of cows to streptococcus and/or other infectious organisms. These organisms are known to enter the mammary systems of cows through the sphincter end of the cow teats usually immediately after milking. Because many cows are assembled together in relatively small confines, and because the same milking equipment is used on more than one cow, these organisms quickly spread from cow to cow throughout the herd. Moreover, because these infectious organisms are also transferred from cow to cow by the common fly, the disease spreads rapidly throughout a cattle herd once a member of the herd has been infected.

Another problem associated with the repeated milking of dairy cows is that the exteriors of the cow teats become chapped and chafed due to repeated handling. Because the cows are left outdoors most of the time, this problem is further aggravated by exposure of the teats to extreme weather conditions, contact with mud and the washings necessitated thereby. Occasionally, chafing and chapping become so acute that the teats actually develop noticeable cuts and abrasions.

In order to alleviate these problems, a number of compositions have been promulgated for treating cow teats to prevent the spread of bovine mastitis and to heal chapped and chafed cow teats. These compositions are water-based and contain a germicidal amount of iodine mixed with minor amounts of lanolin, glycerin or glycol. However, a common drawback associated with these compositions is that they usually contain other ingredients, such as alcohol, to dissolve or disperse the iodine and produce a homogenous composition. Usually, about 5% alcohol is used in such compositions and this, unfortunately, gives the compositions a harsh chapping effect when used over extended periods of time.

It is an object of this invention to provide a composition which effectively controls the spread of bovine mastitis.

It is a further object of this invention to provide a composition which prevents the chafing and chapping of cow teats during repeated milking operations and further aids the healing of cuts and abrasions produced thereby.

It is a still further object of this invention to provide a composition for application to cow teats which can be repeatedly used for long periods of time without harmful side effects.

SUMMARY OF THE INVENTION

These and other objects are accomplished according to the present invention which is based on the discovery that an extremely effective teat dip solution for the control of bovine mastitis can be made by simply agitating together at an elevated temperature a specific amount of iodine in a mineral oil. The iodine oil solution is externally applied to the teats of cows in a dairy herd, and the spread of bovine mastitis in a typical dairy herd is thereby almost totally eliminated. Moreover, the composition of this invention not only prevents the chapping and chafing of cow teats due to repeated milking, but also promotes the healing of teat cuts and abrasions. Finally, the inventive composition has been found to produce no harmful side effects after repeated use extended for periods of time. A still more effective teat dip includes, in addition to the mineral oil and iodine, a small quantity of polyoxyethylene cetyl ether.

DETAILED DESCRIPTION

The unique composition of this invention is made by agitating together up to about 7 weight percent crystalline iodine with an oil at an elevated temperature until the crystalline iodine dissolves and thereafter allowing the composition to cool to ambient. A homogeneous solution of iodine and the oil is thereby produced without the aid of any other dissolving or dispersing agent.

As is known, crystalline iodine is iodine in its elemental form. Any size iodine crystal can be used, but it is preferable to use more finely ground iodine crystals, since they require less agitation to go into solution.

Any oil may be used in the process of this invention so long as it does not react with iodine, for example, animal and vegetable oils, and specifically, peanut oil and corn oil, tung oil or mixtures thereof can be used, although it is preferred to use mineral oils since these oils are relatively inexpensive and appear to be most effective. As is known, "mineral oil" refers to a variety of complex mixtures of hydrocarbons derived from inorganic matter, such as petroleum. While any type of mineral oil may be used in the present invention, it is preferred to use a food or cosmetic grade mineral oil, since these oils are highly pure.

Although neither the viscosity or specific gravity of the oil is critical, it is preferable to use lighter oils since they are more conveniently handled and more conveniently agitated.

In order to make the composition of this invention, the oil and the iodine crystals are simply agitated together at an elevated temperature until the crystals dissolve. This may take from a very short time to many hours since dissolution is dependent not only on the size of the iodine crystals but also the temperature of the composition as well as the particular oil used. Specifically, the larger the iodine crystals, the longer will be the period of agitation, while the higher the temperature, the shorter will be the period of agitation.

As set forth above, the temperature of agitation is dependent on a number of factors, one of which is the oil used. In this regard, it has been found that some oils are capable of dissolving iodine at lower temperatures than other oils. Specifically, it has been found that the minimum temperature at which most oils will dissolve iodine is about 100° F., while the minimum temperature that peanut oil will dissolve iodine is as low as 80° F. Accordingly, the agitation temperature should be at or above these minimum temperatures. The maximum agitation temperature is not critical. However, it has been found that at temperatures above about 180° F., the iodine crystals begin to oxidize. Interestingly, oxidation is manifested in the system by the inability of the oil to dissolve all of the iodine placed therein. As the temperature of agitation increases over 180° F., an increasing proportion of the iodine placed in the oil remains suspended in the oil and is therefore ineffective in controlling bovine mastitis. This phenomenon is more fully illustrated in the following table which shows the effect of increased temperature on the solubility of a given amount of iodine in mineral oil:

| Temperature of Agitation ° F. | Percent of Original Iodine Placed in Oil Which Dissolves |
|---|---|
| 180° | 100 |
| 182° | 97 |
| 184° | 91 |
| 186° | 77 |
| 188° | 61 |
| 190° | 48 |

It should be understood that this table does not show that maximum solubility of iodine in the oils is a function of temperature. Rather, this table shows that the percentage solubility of the iodine is affected by the temperature. In other words, as the temperature of agitation increases, a correspondingly smaller percentage of the original amount of iodine placed in the oil dissolves. This does not mean, however, that higher agitation temperatures cannot be used to make a given solution. On the contrary, this merely means that at temperatures above 180° F., greater portions of the iodine placed in the oil will be wasted. For example, a 1% iodine in mineral oil solution can be made by agitating the components at both 180° and 190° F. However, at 190° F., approximately twice as much iodine must be added to the oil, since only about 48% of the original iodine added will go into solution, the remainder being wasted. Accordingly, it is preferred to keep the agitation temperature below 180° F. in order to minimize the amount of iodine used to make the compositions.

In a preferred embodiment of the invention, the temperature of agitation with most oils is held between about 140° and 180° F. It has been found that the agitation time necessary for complete dissolution is at a minimum between these temperatures, and it is therefore preferable to control the temperature so that the dissolution process occurs as quickly as possible. While the iodine will dissolve in most oils at temperatures between 100° and 140° F., the period of agitation is much longer, and it is therefore not preferred. Moreover, while the iodine will dissolve in the oil at temperatures above 180° F., the unwanted oxidation of iodine wastes too much of the relatively expensive iodine. Correspondingly, when iodine is dissolved in peanut oil, the preferred temperature range is about 100° to 180° F., since agitation time will be at a minimum within this range.

The amount of iodine that may be added to the oil, to provide an effective teat dip, should be from about 0.2 to 7% by weight, preferably from 0.2 to 2% by weight. While the dissolution process of this invention can be used to dissolve iodine in the oil at concentrations outside the broad range, it has been found that at iodine concentrations lower than 0.2%, the compositions have very little germicidal effect, while at iodine concentrations higher than 7%, the compositions may unduly irritate the cow teats. Within this range, however, it has been found that the effectiveness of the composition in controlling bovine mastitis is directly proportional to the amount of iodine in the composition. Additionally, it has been found that compositions whose iodine content is 7% by weight or less not only effectively control the spread of bovine mastitis, but also can be repeatedly used for prolonged periods of time without any harmful side effects.

In one embodiment of the invention instead of heating the entire amount of oil together with the iodine, the iodine is dissolved in a smaller portion of oil to form a concentrated solution. This concentrated solution is then mixed into enough make-up oil to form an iodine/oil solution having the proper concentration. It has been found that when proceeding in this manner, the make-up oil need not be heated to the elevated temperature before the concentrated iodine/oil solution is added thereto. Accordingly, this method of dissolving the iodine in the oil is very inexpensive since it eliminates a portion of the heating costs. Moreover, this method represents a further advantage, since it is possible to dissolve all the iodine in a lower dissolving temperature oil, such as peanut oil, and combine this concentrated solution with a higher dissolving temperature make-up oil, such as mineral oil.

In use, the composition of this invention is merely applied to the exterior of the cow teats. While the frequency of application is not critical, the composition should be applied often enough so that its healing and germicidal effects do not wear off before the next application. It has been found that this can be easily accomplished by applying the composition twice daily, once after each milking.

As set forth above, the inventive process substantially prevents the spreading of bovine mastitis from one cow to another in a dairy herd. In addition, the unique composition of this invention not only substantially prevents chapping and chaffing of the exterior of cow teats due to repeated milking and exposure to extreme weather conditions, but also actually aids in the healing of cuts and abrasions caused thereby. Finally, the composition can be applied over long periods of time without any harmful side effects.

While not wishing to be bound to any theory, it is believed that the unusual results provided by the present composition are due to the penetration of the teat dermis by the oil so that the natural oils washed and worn out from continued daily washing and milking are replaced. Additionally, the iodine is believed to contribute its known germicidal effects to invading streptococcus and/or other infectious organisms to substantially prevent the spread of diseases caused thereby. Furthermore, the composition repels flies, which is believed to reduce the likelihood of transfer of the organisms from cow to cow. Finally, the non-toxic qualities of the composition compared with prior art teat dips are believed to be due to the absence of alcohol or other dissolving or dispersing agents.

While the invention has been completely described above, the following examples are provided to more fully illustrate the method of making the composition of this invention and the method of treating cows with the composition of this invention:

EXAMPLE I

One gallon of technical grade white mineral oil was heated to a temperature of 175° F. and agitated by means of a conventional mixer. 0.0836 Pounds of U.S.P. resublimed iodine in crystal form was added, and agitation was continued until the iodine crystals completely dissolved, about 15 minutes. Agitation and heating were stopped, and the composition was allowed to cool to ambient temperature. The product obtained was approximately 1 gallon of mineral oil containing about 1% by weight iodine completely dissolved therein.

20 Cows were separated from a typical dairy herd and treated with this composition. Treatment was accomplished by dipping the chafed and chapped cow teats into a beaker containing the composition so that the teats were immersed in the composition. The cows were then allowed to rejoin the herd and intermingle with other cows having bovine mastitis. The cows were milked twice daily and care was taken to ensure that streptococcus and other infectious organisms were not transferred from cow to cow during milking. The cows of the test were treated exactly the same way as other cows, except that the above treatment was repeated after each milking. After a period of 8 weeks, it was found that none of the cows treated with the composition of this invention developed bovine mastitis. Further, the chafed and chapped exterior teat skin of the cows treated became soft, smooth, and free of chapping. It was also observed that common flies which tended to fly in close proximity to and land on the teats of untreated cows avoided the teat areas of the treated cows during the entire 8 weeks during which the test lasted.

After 8 weeks, treatment with the iodine/mineral oil solution of this Example was discontinued. The cows were observed for another 8 week period during which the cows were treated exactly the same way as during the original testing period, care being taken not to spread streptococcus and/or other infectious organisms during the twice daily milking. After another 8 weeks, it was observed that five of the cows developed clinical mastitis.

EXAMPLE II

The procedure of Example I was followed except that five different samples of mineral oil were heated to temperatures of 140°, 150°, 160°, 170°, and 180° F. before the iodine was added. Agitation of the five compositions was continued at the initial temperatures to which the mineral oil samples were heated until the iodine completely dissolved in the mineral oil.

The five solutions produced above were all used to treat groups of 20 cows per solution according to the procedure followed in Example I. Each sample was found to be as effective as the composition in Example I.

EXAMPLE III

Five samples were drawn up according to the procedure set forth in Example I in which the concentration of the iodine in the mineral oil was 0.2, 0.4, 0.6, 0.8, and 1.0 weight %. The mineral oil samples were each heated to a temperature of about 180° F. and the various amounts of iodine were added. The compositions were agitated at 180° F. until the iodine was completely dissolved in each sample. A petri dish containing a blood agar medium was streaked with milk samples containing streptococcus. Five small cotton felt pads were each saturated with one of the compositions made in this Example and placed in the petri dish.

After 24 hours, it was observed that streptococcus had rapidly multiplied in all areas of the petri dish except distinct zones surrounding each pad.

The mineral oil-iodine teat dip hereinbefore described can be still further improved by incorporation therein of a small but effective quantity of a polyoxyethylene cetyl ether, e.g., polyoxyethylene (20) cetyl ether. Since the polyoxyethylene cetyl ether is commercially available as a solid, it is first necessary to dissolve it in a liquid carrier such as water before admixing it with the mineral oil-iodine solution. In its commercially available form, which is suitable for use herein, polyoxyethylene cetyl ether contains a small quantity of preservative, such as 0.005% by weight citric acid. However, the citric acid is not necessary to the present invention.

The quantity of polyoxyethylene cetyl ether utilized in the teat dip is in large part immaterial provided that at least 2 grams are present in each gallon of teat dip. Although more of the polyoxyethylene cetyl ether additive may be safely employed, it will be appreciated that the more that is used, the greater is the amount of water necessary to dissolve it. And, since the teat dips of the present invention find utility in those geographic areas which experience ambient temperatures below the freezing point of water, it is desirable to include in the teat dip as little water as possible. Another reason for maintaining the water content of the teat dip as low as possible is that the water and mineral oil will not mix in the absence of an emulsifier. Since the polyoxyethylene cetyl ether performs the emulsifying function, if too much water is added, additional polyoxyethylene cetyl ether may be necessary to assure substantially complete mixing. Thus, it may be said that the water quantity should be at least sufficient to dissolve or liquefy the polyoxyethylene cetyl ether and the polyoxyethylene cetyl ether quantity should be at least 2 grams per gallon of teat dip and at least sufficient to assure substantially complete mixing of the mineral oil and water.

In one preferred form of the invention, the teat dip comprises 95% by volume mineral oil and iodine solution containing the desired concentration of iodine, 5% by volume water and 2 grams of polyoxyethylene cetyl ether.

EXAMPLE IV

A 1500 ml portion of mineral oil having a specific gravity of 0.865 was weighed and found to weigh 1290 grams. To the 1500 ml or 1290 grams of mineral oil was added 6.45 grams of resublimed iodine. The resublimed iodine was mixed with the mineral oil as described in Example I. If all of the 6.45 grams iodine had gone into perfect solution as free iodine, the percent total iodine, by weight, would then be 0.4976. However, a 25 ml portion of this preparation of iodine in mineral oil was assayed, using standard laboratory methods, and it was determined that the free iodine content of the solution was in fact 0.4750%, and was stable upon cooling to ambient temperature. One (1) gram of polyoxyethylene (20) cetyl ether (containing 0.005% citric acid as a preservative) was weighed and added to 75 ml $H_2O$ with mixing until the polyoxyethylene (20) cetyl either was thoroughly in solution with the water. The 75 ml of water ($H_2O$) containing 1 gram polyoxyethylene (20) cetyl ether was added to 1425 ml of the previously prepared iodine-mineral oil solution, and was agitated until thoroughly mixed. The iodine content was then 0.45120% by weight. About 90–95% of the water ($H_2O$) containing 1 gram polyoxyethylene (20) cetyl ether remained in suspension with the iodine mineral oil solution. The balance returned to solution immediately upon mild shaking. Alternatively, the unsuspended balance may be removed by filtration, if desired.

EXAMPLE V

A solution of 0.5% iodine by weight in mineral oil was prepared by the same method as is described in Example I. This preparation was halved, and to one half was added 5% by volume water containing not less than 2 grams of polyoxyethylene (20) cetyl ether per gallon of teat dip.

A preparation of 300 ml of raw skim milk was autoclaved until sterile, and checked for sterility using standard laboratory procedures. To this preparation of sterile raw skim milk was added a $5 \times 10^7$ concentration of staphylococcus aureus.

A number of dairy cows were confined to stanchion in a manner that prevented them from lying down or moving about. Their tails were suspended to avoid accidental contamination of the experimental area. Their udders and teats were washed using a warm water detergent solution, followed by thorough rinsing, followed by drying with single service sanitary paper towels. The entire teat surface and apex end was then scrubbed with a sterile cotton pad soaked in 70% alcohol, and allowed to air dry. The previously prepared solution of sterile raw skim milk containing $5 \times 10^7$ colony forming units of staphylococcus aureus was dipped full length onto each teat of each cow.

Following exposure of the teats of each cow to the staphylococcus aureus preparation, the teats of each cow were allowed to dry for a period of 60 minutes. At this point, two teats of each cow were dipped full length into the previously prepared iodine-mineral oil solutions. The remaining two teats of each cow served as undipped controls. Half of the dipped teats were dipped with the iodine-mineral solution, while the other half were dipped in the iodine-mineral oil solution containing 5% by volume water and polyoxyethylene cetyl ether. One hour (60 minutes) after dipping the teats of each cow in the iodine-mineral oil solutions, each teat of each cow was scrubbed with a separate and individual swab from a number of sterile disposable Falcon Swube 2009 swab tubes prepared by adding to each tube one (1) ml of sterile raw skim milk containing sodium thiosulfate as a quencher.

The swab tubes were immediately returned to the laboratory for plating of the recovery solution from each tube onto selective media culture plates. Following standard laboratory procedures, the recovery solution was streaked onto selective media plates, using one plate to represent one teat/swab tube. The plates and tubes had matched markings for identification purposes. After 24 hours incubation at 37° C., the number of recovered colonies of staphylococcus aureus on each plate were counted, and the recovery from the undipped controls were compared to the recovery from the dipped teats.

The results of these tests are set forth in the following Tables:

| | COMPARISON OF STAPHYLOCOCCUS AUREUS COUNTS FROM UNDIPPED CONTROL TEATS AND FROM TEATS DIPPED IN MINERAL OIL - 0.5% IODINE SOLUTION | |
|---|---|---|
| | CONTROLS TEATS | DIPPED TEATS |
| No.-1 | 39,320 | 1,873 |
| No.-2 | 37,678 | 2,268 |
| No.-3 | 32,461 | 1,946 |
| No.-4 | 36,517 | 1,949 |
| AVERAGE | 36,494 | 2,009 |
| % REDUCTION FROM CONTROLS | | 89.01% |

| | COMPARISON OF STAPHYLOCOCCUS AUREUS COUNTS FROM UNDIPPED CONTROL TEATS AND FROM TEATS DIPPED IN MINERAL OIL - 0.5% IODINE SOLUTION CONTAINING POLYOXYETHYLENE CETYL ETHER | |
|---|---|---|
| | CONTROL TEATS | DIPPED TEATS |
| No.-1 | 42,595 | 298 |
| No.-2 | 54,230 | 376 |
| No.-3 | 45,298 | 340 |
| No.-4 | 47,362 | 302 |
| AVERAGE | 47,362 | 329 |
| % REDUCTION FROM CONTROLS | | 99.36% |

Notwithstanding that the performance of the iodine-mineral oil preparation should be considered efficacious, the product with the added polyoxyethylene cetyl ether and water was superior.

While the present invention has been described with reference to particular embodiments thereof, it will be understood that numerous modifications can be made by those skilled in the art without actually departing from the scope of the invention. Accordingly, all modifications and equivalents may be resorted to which fall wthin the scope of the invention as claimed.

What is claimed as new is as follows:
1. A process for treating cows to control the spread of bovine mastitis, prevent chapping and chafing of cow teats and aid the healing of teat cuts and abrasions comprising applying to the cow teats a composition consisting essentially of mineral oil containing 0.2 to 7% by weight iodine dissolved therein.

2. A process, as claimed in claim 1, wherein said oil contains from 0.5 to 1% by weight iodine.

3. A process, as claimed in claim 1, wherein said composition is applied to the cow teats following milking of the cow.

4. A process, as claimed in claim 3, wherein said composition is applied to the cow teats by dipping said teats in said composition.

5. A process, as claimed in claim 1, wherein said composition further includes not less than 2 grams per gallon of composition of polyoxyethylene cetyl ether and at least sufficient water to dissolve said polyoxyethylene cetyl ether.

6. A process, as claimed in claim 5, wherein said oil contains from 0.5 to 1% by weight iodine.

7. A process, as claimed in claim 5, wherein said composition is applied to the cow teats following milking of the cow.

8. A process, as claimed in claim 7, wherein said composition is applied to the cow teats by dipping said teats in said composition.

9. A teat dip for controlling the spread of bovine mastitis consisting essentially of mineral oil, about 0.2 to 7% by weight iodine dissolved in said oil, not less than 2 grams per gallon teat dip of polyoxyethylene cetyl ether, and at least sufficient water to dissolve said polyoxyethylene cetyl ether.

10. A teat dip, as claimed in claim 9, wherein said teat dip contains about 0.2 to 2% by weight iodine.

11. A teat dip, as claimed in claim 9, wherein said teat dip contains about 0.5 to 1% by weight iodine.

12. A teat dip, as claimed in claim 11, wherein said teat dip contains about 1% by weight iodine.

13. A teat dip, as claimed in claim 9, wherein said mineral oil is selected from food and cosmetic grade mineral oils.

14. A teat dip, as claimed in claim 13, wherein said mineral oil is a food grade mineral oil.

15. A teat dip, as claimed in claim 9, wherein said mineral oil-iodine solution comprises about 95% by volume of said dip.

16. A teat dip, as claimed in claim 15, wherein said teat dip contains about 0.2 to 2% by weight iodine.

* * * * *